US00PP16004P2

(12) United States Plant Patent
Van Andel

(10) Patent No.: US PP16,004 P2
(45) Date of Patent: Sep. 27, 2005

(54) *SPATHIPHYLLUM* PLANT NAMED 'NR. 256'

(50) Latin Name: ***Spathiphyllum* sp**
Varietal Denomination: Nr. 256

(75) Inventor: Otto Jan Robert Van Andel, De Kwakel (NL)

(73) Assignee: Braam Young Plants B.V., De Kwakel (NL)

( * ) Notice: Subject to any disclaimer, the term of this patent is extended or adjusted under 35 U.S.C. 154(b) by 18 days.

(21) Appl. No.: 10/915,055

(22) Filed: Aug. 10, 2004

(51) Int. Cl.[7] ..... A01H 5/00
(52) U.S. Cl. ..... Plt./364
(58) Field of Search ..... Plt./364

*Primary Examiner*—Anne Marie Grunberg
(74) *Attorney, Agent, or Firm*—C. A. Whealy

(57) ABSTRACT

A new and distinct cultivar of *Spathiphyllum* plant named 'Nr. 256', characterized by its compact, upright and outwardly arching plant habit; freely clumping growth habit; glossy dark green-colored leaves; white-colored spathes and creamy white-colored spadices that are positioned above the foliage on strong and erect scapes; and good postproduction longevity.

1 Drawing Sheet

Botanical classification: *Spathiphyllum* sp.

BACKGROUND OF THE INVENTION

The present Invention relates to a new and distinct cultivar of *Spathiphyllum* plant, botanically known as *Spathiphyllum* hybrid, and hereinafter referred to by the cultivar name Nr. 256.

The new cultivar is a product of a planned and controlled breeding program conducted by the Inventor in De Kwakel, The Netherlands. The objective of the breeding program is to create new compact *Spathiphyllum* cultivars with dark green foliage and strong flower scapes.

The new cultivar originated from a cross-pollination made by the Inventor in January, 2001 of the *Spathiphyllum* hybrid cultivar Cissy, not patented, as the female or seed parent and the *Spathiphyllum* hybrid cultivar Nr. 336, not patented, as the male or pollen parent. The cultivar Nr. 256 was discovered and selected by the Inventor as a single plant within the progeny of the stated cross-pollination in a controlled environment in De Kwakel, The Netherlands.

Asexual propagation of the new cultivar by tissue culture since January, 2002, in a laboratory in De Kwakel, The Netherlands, has shown that the unique features of this new *Spathiphyllum* plant are stable and reproduced true to type in successive generations of asexual propagation.

SUMMARY OF THE INVENTION

The new *Spathiphyllum* has not been observed under all possible environmental conditions. The phenotype may vary somewhat with variations in environment such as temperature and light intensity without, however, any variance in genotype.

The following traits have been repeatedly observed and are determined to be the unique characteristics of 'Nr. 256'. These characteristics in combination distinguish 'Nr. 256' as a new and distinct *Spathiphyllum* cultivar:

1. Compact, upright and outwardly arching plant habit.
2. Freely clumping growth habit.
3. Glossy dark green-colored leaves.

4. White-colored spathes and creamy white-colored spadices that are positioned above the foliage on strong and erect scapes.
5. Good postproduction longevity.

Plants of the new *Spathiphyllum* can be compared to plants of the female parent, the cultivar Cissy. In side-by-side comparisons conducted in De Kwakel, The Netherlands, plants of the new *Spathiphyllum* differed from plants of the cultivar Cissy in the following characteristics:

1. Plants of the new *Spathiphyllum* were more compact than plants of the cultivar Cissy.
2. Leaves of plants of the new *Spathiphyllum* were broader and darker green in color than leaves of plants of the cultivar Cissy.
3. Plants of the new *Spathiphyllum* had shorter leaf petioles than plants of the cultivar Cissy.

Plants of the new *Spathiphyllum* can be compared to plants of the male parent, the cultivar Nr. 336. In side-by-side comparisons conducted in De Kwakel, The Netherlands, plants of the new *Spathiphyllum* differed from plants of the cultivar Nr. 336 in the following characteristics:

1. Plants of the new *Spathiphyllum* were more compact and more freely clumping than plants of the cultivar Nr. 336.
2. Plants of the new *Spathiphyllum* were bushier than plants of the cultivar Nr. 336.
3. Leaves of plants of the new *Spathiphyllum* were narrower and darker green in color than leaves of plants of the cultivar Nr. 336.
4. Plants of the new *Spathiphyllum* had shorter leaf petioles than plants of the cultivar Nr. 336.

Plants of the new *Spathiphyllum* can also be compared to plants of the *Spathiphyllum* cultivar Petite, not patented. However, in side-by-side comparisons conducted in De Kwakel, The Netherlands, plants of the new *Spathiphyllum* differed from plants of the cultivar Petite in the following characteristics:

1. Plants of the new *Spathiphyllum* were more freely clumping than plants of the cultivar Petite.
2. Plants of the new *Spathiphyllum* were bushier than plants of the cultivar Petite.

3. Plants of the new *Spathiphyllum* had narrower and darker green-colored leaves than plants of the cultivar Petite.
4. Plants of the new *Spathiphyllum* had shorter leaf petioles than plants of the cultivar Petite.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new *Spathiphyllum.*

The photograph at the top of the sheet comprises a side perspective view of a typical plant of 'Nr. 256' grown in a container.

The photograph at the bottom left of the sheet is a close-up view of upper and lower surfaces of typical leaves of 'Nr. 256'.

The photograph at the bottom right of the sheet is a close-up view of a typical inflorescence of 'Nr. 256'.

DETAILED BOTANICAL DESCRIPTION

The aforementioned photographs and following observations and measurements describe five month old plants (from planting rooted tissue-cultured plantlets) grown in De Kwakel, The Netherlands, in a glass-covered greenhouse and under commercial production conditions in 12-cm containers with one plant per container. During the production of the plants, day temperatures were about 22° C., night temperatures were about 19° C. and light levels were about 20,000 to 28,000 lux.

In the following description, color references are made to The Royal Horticultural Society Colour Chart, 1995 Edition, except where general terms of ordinary dictionary significance are used.

Botanical classification: *Sphathiphyllum* hybrid cultivar Nr. 256.

Parentage:

*Female parent.*—*Spathiphyllum* hybrid cultivar Cissy, not patented.

*Male parent.*—*Spathiphyllum* hybrid cultivar Nr. 336, not patented.

Propagation:

*Type.*—By tissue culture.

*Time to initiate roots on a tissue-cultured cutting.*—Summer: About 11 days at 24° C. Winter: About 15 days at 22° C.

*Time to produce a fully-rooted tissue-cultured plantlet.*—Summer: About 14 weeks at 22° C. Winter: About 16 weeks at 22° C.

*Root description.*—Primary roots, thick and fleshy; lateral branch roots, finer; primary and lateral roots white in color and abundant.

Plant description:

*Plant shape.*—Compact, upright and outwardly arching plant habit; inverted triangle.

*Growth habit.*—Erect when young, becoming outwardly arching as leaves develop. Freely clumping and bushy full appearance; about 50 leaves per plant; moderately vigorous.

*Plant height.*—About 32 cm from soil level to top of leaf plane and about 54 cm from soil level to spathe apices.

*Plant spread.*—About 42 cm.

*Foliage description.*—Length: About 14 to 20 cm. Width: About 4 to 8 cm. Shape: Lanceolate. Apex: Apiculate. Base: Attenuate to cuneate. Margin: Entire. Aspect: Initially upright, then outwardly arching. Surface: Midrib and lateral veins sunken on upper surface and prominent on lower surface; upper surface of blade convex between veins, lower surface of blade concave between veins; upper and lower surfaces rugose. Texture, upper and lower surfaces: Somewhat leathery; glabrous and smooth. Luster, upper surface: Glossy. Luster, lower surface: Semi-glossy. Venation pattern: Pinnate. Color: Developing leaves, upper surface: Close to 137B. Developing leaves, lower surface: Close to 138B. Fully expanded leaves, upper surface: 147A. Fully expanded leaves, lower surface: Close to 147B. Midvein and lateral veins, upper surface: Close to 146B. Midvein and lateral veins, lower surface: Close to 146D. Petiole: Length: About 5 to 15 cm. Diameter, just below the geniculum: About 4 mm. Diameter, at soil level: About 5 mm. Geniculum length: About 1.5 to 3 cm. Geniculum diameter: About 2 to 4 mm. Geniculum aspect: Straight. Color: Petiole: 146C to 146D. Geniculum: 146C to 146D.

Inflorescence description:

*Inflorescence arrangement/quantity.*—Concave spathes with spadices held above the foliage on strong and erect scapes. About one or two open spathes per plant at one time; inflorescences arise from the petiole sheath.

*Natural flowering season.*—Spring through the summer in The Netherlands. Inflorescences persistent.

*Inflorescence longevity.*—Spathes generally maintain white color for about six weeks on the plant.

*Fragrance.*—None detected.

*Inflorescence buds.*—Length: About 6 cm. Diamater: About 1 cm. Shape: Columnar. Color: Close to 155A.

*Spathe.*—Length: About 6 to 15 cm. Width: About 2.5 to 6.5 cm. Shape: Broadly lanceolate. Apex: Apiculate; twisting. Base: Cuneate. Aspect: Concave. Texture, front and rear surfaces: Slightly leathery; glabrous and smooth; slightly rugose. Color: When developing, front and rear surfaces: 155A. Fully opened, front and rear surfaces: 155D; after senescence, color becoming closer to 145C. Venation, front surface: 155A. Venation, rear surface: Midvein, 144A; lateral veins, 155A.

*Spadix.*—Length: About 1.5 to 4 cm. Diameter: About 1.3 cm. Shape: Columnar with obtuse apex. Aspect: Mostly straight. Color: 158A.

*Flowers.*—Quantity per spadix: About 55 to 120. Diameter: About 2 mm. Shape: Conical. Color: 158D. Staminate flowers: Anther color: 158D. Amount of pollen: Moderate. Pollen color: 159A. Pistillate flowers: Shape: Conical; pistillate flowers extend beyond the staminate flowers. Stigma color: 158B to 158C. Ovary color: 158B to 158C.

*Scapes.*—Length: About 20 to 35 cm. Diameter: About 3.5 mm. Aspect: Erect. Strength: Strong. Color: 146A.

*Fruit/seed.*—Fruit and seed production have not been observed.

Disease/pest resistance: Plants of the new *Spathiphyllum* have not been observed to be resistant to pathogens or pests common to *Spathiphyllum.*

Temperature tolerance: Plants of the new *Spathiphyllum* have been observed to tolerate temperatures from 14 to 27° C.

It is claimed:

1. A new and distinct cultivar of *Spathiphyllum* plant named 'Nr. 256', as illustrated and described.

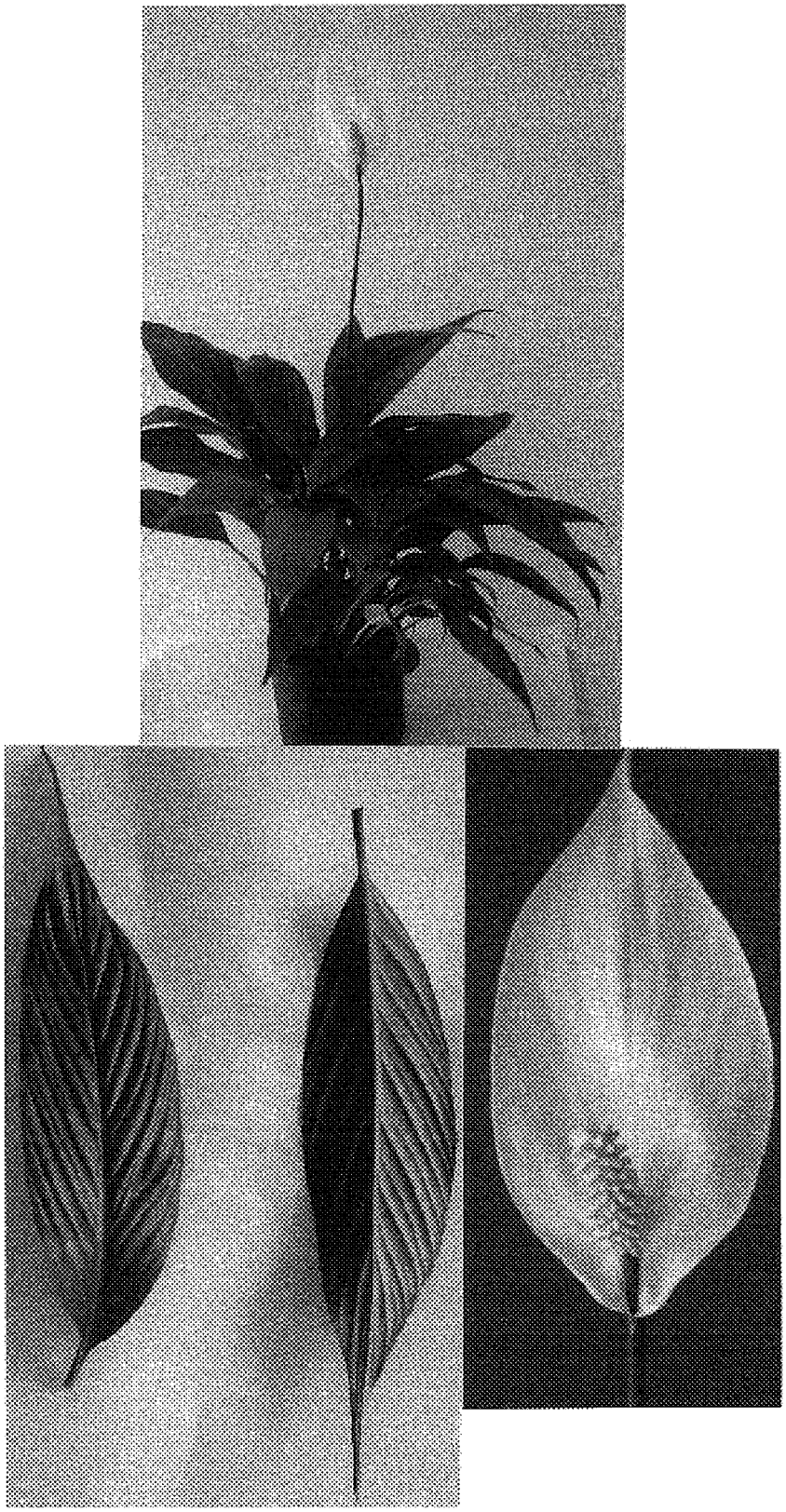

* * * * *